United States Patent [19]

Müller et al.

[11] Patent Number: 5,204,374
[45] Date of Patent: Apr. 20, 1993

[54] CYCLOALKANO(B)DIHYDROINDOLES AND -INDOLESULPHONAMIDES SUBSTITUTED BY HETEROCYCLES

[75] Inventors: Ulrich E. Müller; Ulrich Rosentreter, both of Wuppertal; Ulrich Niewöhner, Wermelskirchen; Elisabeth Perzborn, Wuppertal; Erwin Bischoff, Wuppertal; Hans-Georg Dellweg, Wuppertal, all of Fed. Rep. of Germany; Peter Norman, Slough, United Kingdom; Nigel J. Cuthbert, Great Missenden, United Kingdom; Hilary P. Francis, Woodley, United Kingdom

[73] Assignee: Bayer Aktiengesellschaft, Leverkusen, Fed. Rep. of Germany

[21] Appl. No.: 679,710

[22] Filed: Apr. 3, 1991

[30] Foreign Application Priority Data

Apr. 10, 1990 [GB] United Kingdom ............... 9008108

[51] Int. Cl.$^5$ ............... C07D 215/36; C07D 209/82; A01N 43/54; A01N 43/38
[52] U.S. Cl. ............................. 514/209; 514/312; 514/323; 514/339; 514/369; 514/372; 514/398; 514/411; 546/153; 546/155; 546/200; 546/272; 548/181; 548/213; 548/225; 548/226; 548/243; 548/439; 548/440; 548/441; 548/442; 548/443; 548/448; 548/449; 548/311.4
[58] Field of Search ............... 546/272, 153, 155, 200; 548/444, 439, 443, 181, 213, 225, 228, 243, 336, 440, 441, 442, 448, 449; 514/269, 312, 323, 339, 369, 372, 376, 398, 411

[56] References Cited

U.S. PATENT DOCUMENTS

| | | | |
|---|---|---|---|
| 3,946,021 | 3/1976 | Albrecht et al. | 548/444 |
| 3,975,398 | 8/1976 | Werner et al. | 548/444 |
| 4,464,379 | 8/1984 | Betzing et al. | |

FOREIGN PATENT DOCUMENTS 0201735 11/1986 European Pat. Off.
0242518 10/1987 European Pat. Off.
0242767 10/1987 European Pat. Off.
0310179 4/1989 European Pat. Off.

Primary Examiner—C. Warren Ivy
Assistant Examiner—Raymond Covington
Attorney, Agent, or Firm—Sprung Horn Kramer & Woods

[57] ABSTRACT

New cycloalkano[b]dihydroindoles and -indolesulphonamides, substituted by heterocycles, of the formula (I)

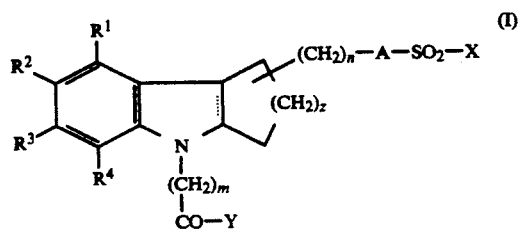

in which $R^1$, $R^2$, $R^3$ and $R^4$ are identical or different and represent hydrogen, nitro, cyano, halogen, trifluoromethyl, carboxyl, hydroxyl or trifluoromethoxy, or represent a group of the formula $-S(O)_w R^5$, in which
  $R^5$ denotes alkyl or optionally substituted aryl,
  w denotes the number 0, 1 or 2, or
  represents alkoxy or alkoxycarbonyl, or benzyloxy, or
  represents a group of the formula $-NR^6R^7$, in which
    $R^6$ and $R^7$ are identical or different and
      denote hydrogen, alkyl or acyl or
      denote aryl, or
      denote a group of the formula $-S(O)_w R^5$, in which $R^5$ and w have the abovementioned meaning,
      represent cycloalkyl or
      represent optionally substituted alkyl or alkenyl,
m represents the number 1, 2, 3 or 4,
n represents the number 0, 1 or 2,
z represents the number 1, 2, 3 or 4,
A represents a bond or the —NH group, (Abstract continued on next page.)

X represents an optionally substituted heterocycle,

Y represents hydroxyl, alkoxy, phenoxy or a group of the formula $-NR^6R^7$, in which $R^6$ and $R^7$ have the abovementioned meaning, an isomeric form thereof or salts thereof are useful to treat thromboembolisms, ischaemias, asthma and allergies. Processes of making and chemical intermediates are also disclosed.

14 Claims, No Drawings

CYCLOALKANO(B)DIHYDROINDOLES AND -INDOLESULPHONAMIDES SUBSTITUTED BY HETEROCYCLES

The invention relates to new cycloalkano[b]dihydroindoles and -indolesulphonamides substituted by heterocycles, to processes for their preparation and to their use in medicaments.

It is already known that cycloalkano[b]dihydroindoles and -indolesulphonamides have a thrombocyte aggregation-inhibiting action [compare DOS (German Offenlegungsschrift) 3,631,824].

Ne cycloalkano[b]dihydroindoles and -indolesulphonamides, substituted by hetrocycles, of the general formula (I)

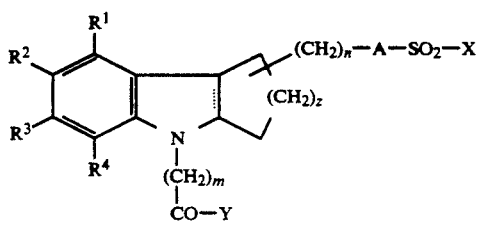

in which $R^1$, $R^2$, $R^3$ and $R^4$ are identical or different and represent hydrogen, nitro, cyano, halogen, trifluoromethyl, carboxyl, hydroxyl or trifluoromethoxy, or represent a group of the formula —S(O)$_w$R$^5$, in which
  $R^5$ denotes straight-chain or branched alkyl having up to 8 carbon atoms or aryl having 6 to 10 carbon atoms, which, for its part, is optionally substituted by halogen, nitro, cyano or trifluoromethyl,
  w denotes the number 0, 1 or 2, or
  represents straight-chain or branched alkoxy or alkoxycarbonyl in each case having up to 10 carbon atoms, or benzyloxy, or
  represents a group of the formula —NR$^6$R$^7$, in which
    $R^6$ and $R^7$ are identical or different and
      denote hydrogen, straight-chain or branched alkyl or acyl in each case having up to 8 carbon atoms or
      denote aryl having 6 to 10 carbon atoms, or
      denote a group of the formula —S(O)$_w$R$^5$, in which $R^5$ and w have the abovementioned meaning,
      represent cycloalkyl having 3 to 8 carbon atoms or
      represent aryl having 6 to 10 carbon atoms, or
      represent straight-chain or branched alkyl or alkenyl in which case having up to 10 carbon atoms, which are optionally substituted by halogen, hydroxyl, carboxyl, cyano, aryl having 6 to 10 carbon atoms, straight-chain or branched alkyl, alkoxy or alkoxycarbonyl in each case having up to 8 carbon atoms or by a group of the formula

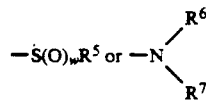

in which w, $R^5$, $R^6$ and $R^7$ have the abovementioned meaning, m represents the number 1, 2, 3 or 4,
n represents the number 0, 1 or 2,
z represents the number 1, 2, 3 and 4,
A represents a bond or the —NH group,
X represents a heterocycle having heteroatoms from the series comprising nitrogen, sulphur or oxygen, which is optionally monosubstituted to trisubstituted by identical or different substituents from the series comprising halogen, trifluoromethyl, trifluoromethoxy, straight-chain or branched alkyl or alkoxy having up to 8 carbon atoms, phenyl or by a group of the formula —S-(O)$_w$—R$^5$ or —NR$^6$R$^7$, in which $R^5$, $R^6$, $R^7$ and w have the abovementioned meaning,
Y represents hydroxyl, alkoxy having up to 8 carbon atoms, phenoxy or a group of the formula —NR$^6$R$^7$, in which
  $R^6$ and $R^7$ have the abovementioned meaning, if appropriate in an isomeric form, and their salts, have now been found.

The cycloalkano[b]dihydroindoles and -indolesulphonamides substituted by heterocycles, according to the invention, have one or more asymmetric carbon atoms and can therefore exist in various stereochemical forms. Regioisomers may also occur. The invention relates both to the individual isomers and to their mixtures.

The compounds according to the invention exist in stereoisomeric forms which behave either as image and mirror image (enantiomers) or which do not behave as image and mirror image (diastereomers). The invention relates both to the antipodes and to the racemic modifications and the diastereomer mixtures. The racemic modifications, like the diastereomers, can be separated into the stereoisomerically uniform constituents in a known manner (compare E. L. Eliel, Stereochemistry of Carbon Compounds, McGraw Hill, 1962).

The cycloalkano[b]dihydroindoles and -indolesulphonamides substituted by heterocycles, according to the invention, can also be present in the form of their salts. In general, salts with organic or inorganic bases or acids may be mentioned here.

In the context of the present invention, physiologically acceptable salts are preferred. Physiologically acceptable salts of the cycloalkano[b]dihydroindoles and -indolesulphonamides substituted by heterocycles can be metal salts or ammonium salts of the substances according to the invention which have a free carboxyl group. Particularly preferred salts are, for example, sodium, potassium, magnesium or calcium salts, and also ammonium salts which are derived from ammonia or organic amines, such as, for example, ethylamine, di- or triethylamine, di- or triethanolamine, dicyclohexylamine, dimethylaminoethanol, arginine, lysine or ethylenediamine.

Physiologically acceptable salts may also be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

Heterocycle in general represents a 5- to 7-membered, preferably 5- to 6-membered, saturated or unsaturated ring which can contain up to two oxygen, sulphur and/or nitrogen atoms as heteroatoms and to which further aromatic or heterocyclic rings can be fused.

5- and 6-membered rings having an oxygen, sulphur and/or up to two nitrogen atoms are preferred, which may also be fused to benzene.

The following are mentioned as preferred: thienyl, furyl, pyrrolyl, pyrazolyl, pyridyl pyrimidyl, pyrazinyl, pyridazinyl, quinolyl, isoquinolyl, quinazolyl, quinoxazolyl, cinnolyl, thiazolyl, benzothiazolyl, isothiazolyl, benzisothiazolyl, oxazolyl, benzoxazolyl, isoxazolyl, imidazolyl, benzimidazolyl indolyl, morpholinyl, pyrrolidinyl, piperidyl or piperazinyl. azinyl.

The substances according to the invention surprisingly show a thrombocyte aggregation-inhibiting action, and additionally cause an inhibition of thromboxane synthase in isolated platelets and can be used for the therapeutic treatment of humans and animals.

Preferred compounds of the general formula (I) are those in which $R^1$, $R^2$, $R^3$ and $R^4$ are identical or different and represent hydrogen, fluorine, chlorine, bromine, iodine, nitro, cyano, trifluoromethyl, trifluoromethoxy, straight-chain or branched alkyl or alkoxy in each case having up to 6 carbon atoms, or phenyl, or represent a group of the formula $-NR^6R^7$, in which $R^6$ and $R^7$ are identical or different and denote hydrogen, straight-chain or branched alkyl having up to 6 carbon atoms or phenyl, or represent a group of the formula $-S(O)_wR^5$, in which $R^5$ denotes straight-chain or branched alkyl having up to 6 carbon atoms, or phenyl, and w denotes the number 0 or 2, m represents the number 1, 2 or 3, n represents the number 0 or 1, z represents the number 1, 2 or 3, A represents a direct bond or the —NH group, X represents pyridyl, pyrimidyl, pyridazyl, quinolyl, morpholinyl, piperidinyl, thienyl, pyrryl, oxazolyl, isoxazolyl, imidazolyl, thiazolyl or isothiazolyl, which are optionally monosubstituted or disubstituted by identical or different substituents from the series comprising fluorine, chlorine, bromine, trifluoromethyl, trifluoromethoxy, hydroxyl or straight-chain or branched alkyl having up to 6 carbon atoms, Y represents hydroxyl, alkoxy having up to 6 carbon atoms, phenoxy or a group of the formula $-NR^6R^7$, in which $R^6R^7$ have the abovementioned meaning, if appropriate in an isomeric form, and their salts.

Particularly preferred compounds of the general formula (I) are those in which $R^1$, $R^2$, $R^3$ and $R^4$ are identical or different and represent hydrogen, fluorine, chlorine, trifluoromethyl or trifluoromethoxy or straight-chain or branched alkyl having up to 4 carbon atoms.

m represents the number 1 or 2, n represents the number 0 to 1, z represents the number 1 or 2, A represents the —NH group X represents pyridyl, thienyl, pyrryl, imidazolyl, isothiazolyl or thiazolyl, which are optionally substituted by fluorine, chlorine, bromine, trifluoromethyl, trifluoromethoxy or straight-chain or branched alkyl having up to 4 carbon atoms, Y represents hydroxyl, alkoxy having up to 4 carbon atoms, phenoxy or a group of the formula $-NR^6R^7$, in which $R^6$ and $R^7$ are identical or different and denote hydrogen or straight-chain or branched alkyl having up to 4 carbon atoms, if appropriate in an isomeric form, and their salts.

Cycloalkano[b]indolesulphonamides are very particularly preferred.

The compounds of the general formula (I)

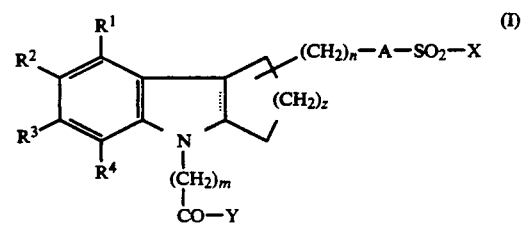

in which $R^1$, $R^2$, $R^3$, $R^4$, A, X, Y, m, n and z have the abovementioned meaning, can be prepared by a process in which

[A] in the case in which m represents the number 2, compounds of the general formula (II)

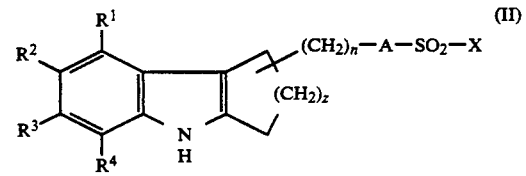

in which $R^1$, $R^2$, $R^3$, $R^4$, A, X, n and z have the abovementioned meaning, are reacted first with acrylonitrile in inert solvents to give the corresponding cyanoethyl compounds, if appropriate in the presence of a base, and then hydrolyzed by a customary method to give the corresponding acids (Y=OH), or by a process in which

[B] compounds of the general formula (III)

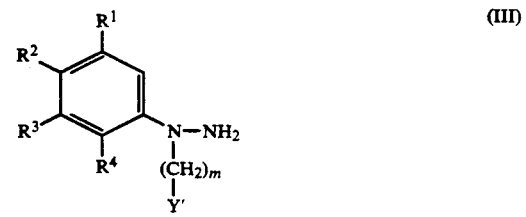

in which $R^1$, $R^2$, $R^3$, $R^4$ and m have the abovementioned meaning, and

Y'-represents carboxyl, ($C_1$-$C_4$)-alkoxycarbonyl or cyano, are reacted directly with cycloalkanonesulphonamides of the general formula (IV)

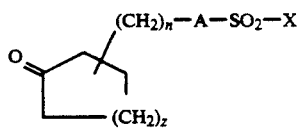  (IV)

in which z, n, A and X have the abovementioned meaning, in inert solvents, if appropriate in the presence of a catalyst, or

[C] compounds of the general formula (III) are reacted first with compounds of the general formula (IVa)

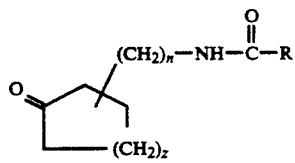  (IVa)

in which z and n have the abovementioned meaning, and

R represents straight-chain or branched $(C_1-C_8)$-alkyl or phenyl, with subsequent hydrolysis, to give compounds of the general formula (V)

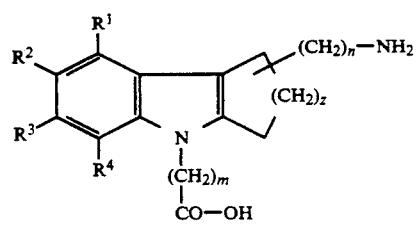  (V)

in which $R^1$, $R^2$, $R^3$, $R^4$, m, n and z have the abovementioned meaning, and in a further step are sulphonated with sulphonyl halides of the general formula (VI)

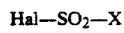  (VI)

Hal—SO₂—X in which

X has the abovementioned meaning and

Hal represents fluorine, chlorine or bromine, preferably chlorine,

[D] or in the case in which m represents the number 2, and A denotes the —NH group, phenylhydrazines of the general formula (IIIa)

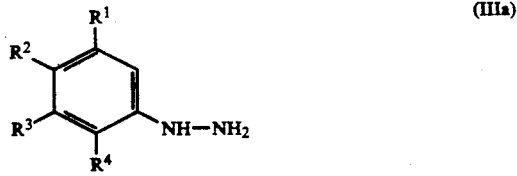  (IIIa)

in which $R^1$, $R^2$, $R^3$ and $R^4$ have the abovementioned meaning, are first reacted with the abovementioned compounds of the general formula (IV) or (IVa) and subsequently with acrylonitrile, then the cyanoethyl compounds are hydrolysed to the corresponding carboxylic acids and in the case of the compounds of the general formula (IVa) sulphonated in a further step with the compounds of the general formula (VI) and additionally in the process [B] and [C] in the case of the acids (Y=OH), the esters or nitriles are hydrolysed by a customary method, in the case of the variation of the esters (Y=alkoxy, $C_1-C_8$-phenoxy), the acids are esterified with the appropriate alcohols in the presence of a catalyst according to a customary method, if appropriate in inert solvents, in the case of the amides and sulphonamides (Y=—$NR^6R^7$, —NH-$SO_2$—$R^5$), either the esters directly or the acids, after customary activation, are reacted with the amines or sulphonamides of the general formulae (VIIa) and (VIIb)

  $HNR^6R^7$ (VIIa)

  $NH_2$—$SO_2$—$R^5$ (VIIb)

in which $R^5$, $R^6$ and $R^7$ have the abovementioned meaning, if appropriate in the presence of a catalyst, and in the case of the cycloalkano[b]dihydroindolesulphonamides, the cycloalkano[b]indolesulphonamides are reduced in inert solvents in the presence of a reducing agent, if appropriate the isomers are separated and in the case of the preparation of the salts, reacted with an appropriate base or acid.

The processes according to the invention can be illustrated by way of example by the following equations:

[A]

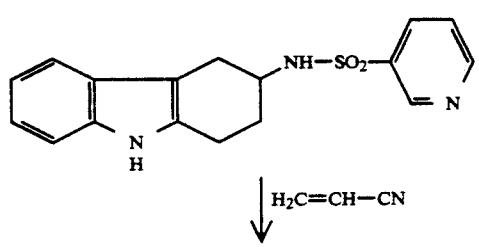

H₂C=CH—CN

-continued
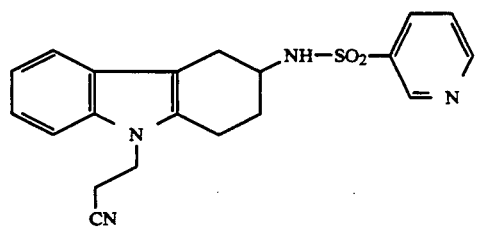
↓ hydrolysis
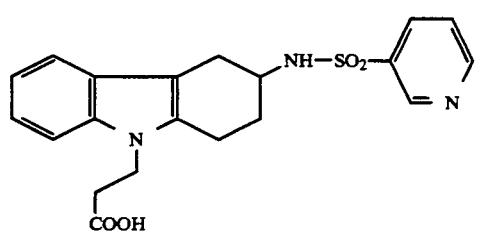
↓ reduction
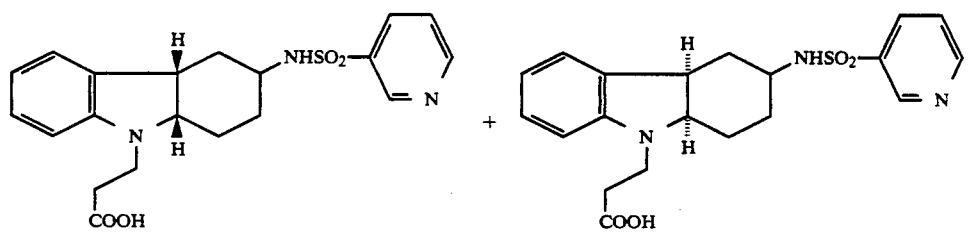
[B]
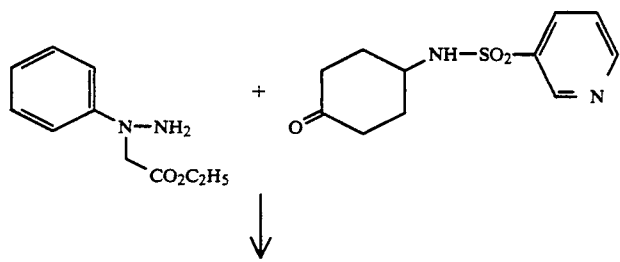
↓
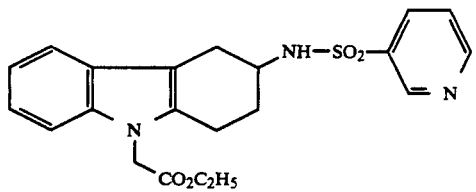
↙ + NH₃       ↘ 1) NaOH  2) HCl
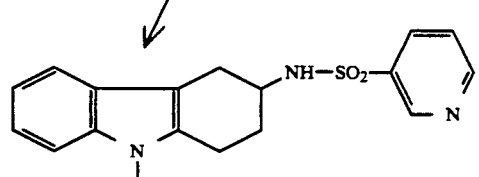   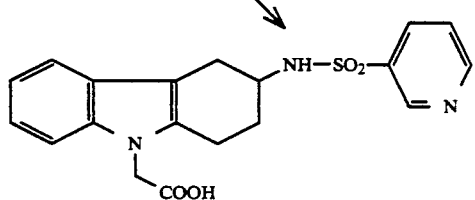

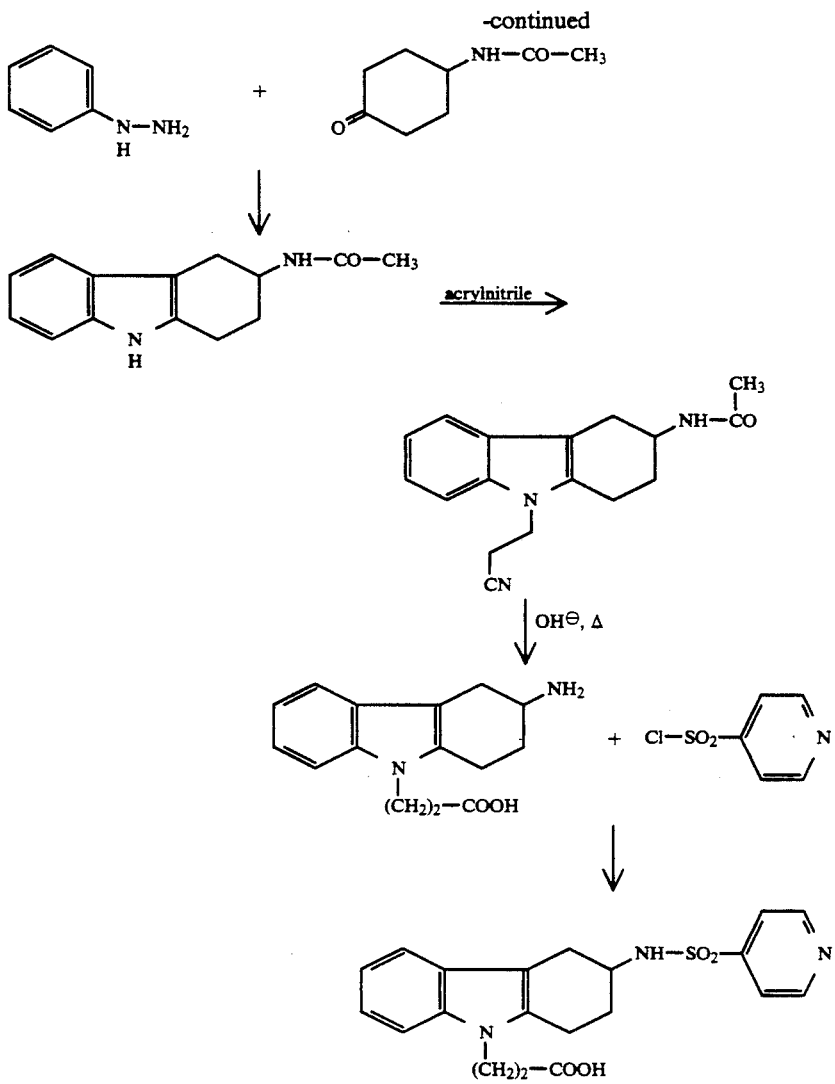

Possible solvents for processes [A] to [D] according to the invention are water or organic solvents which do not change under the reaction conditions. These preferably include chlorinated hydrocarbons, such as, for example, chloroform or methylene chloride, alcohols such as methanol, ethanol, propanol or isopropanol, ethers such as diethyl ether, tetrahydrofuran, dioxane, glycol monomethyl ether or glycol dimethyl ether, hydrocarbons such as benzene, toluene, xylene, cyclohexane, pentane or mineral oil fractions, dimethyl sulphoxide, dimethyl formamide, hexamethylphosphoramide, ethyl acetate, acetonitrile or pyridine. It is also possible to use mixtures of the solvents mentioned.

Possible bases for processes [A] to [D] according to the invention are customary basic compounds. These preferably include alkali metal hydroxides and alkaline earth metal hydroxides such as lithium hydroxide, sodium hydroxide, potassium hydroxide or barium hydroxide, alkali metal hydrides such as sodium hydride, alkali metal carbonates or alkaline earth metal carbonates such as sodium carbonate, potassium carbonate, or alkali metal alkoxides such as, for example, sodium methoxide or sodium ethoxide, potassium methoxide, potassium ethoxide or potassium tert.-butoxide or amides such as sodium amide or lithium diisopropylámide, or organic amines or ammonium salts such as benzyltrimethylammonium hydroxide, tetrabutylammonium hydroxide, pyridine, triethylamine or N-methylpiperidine.

Processes [A] to [D] according to the invention are in general carried out in a temperature range from −20° C. to +150° C.

In general, processes [A] to [D] are carried out at normal pressure. However, it is also possible to work at elevated pressure or at reduced pressure (for example from 0.5 to 5 bar).

The nitriles are hydrolysed in a manner known per se in water or in one of the abovementioned solvents, such as, for example, ethanol, isopropanol, ethylene glycol or glyme or their mixtures, in the presence of bases, acids, hydrogen peroxide or alkali metal or alkaline earth metal peroxides, if appropriate in catalytic amounts.

Suitable peroxides are, for example, sodium peroxide or barium peroxide.

Suitable bases are alkaline earth metal hydroxides or alkali metal hydroxides, such as, for example, sodium hydroxide, potassium hydroxide or barium hydroxide. Sodium hydroxide is preferred.

Suitable acids are the customary acids. These preferably include inorganic acids such as hydrochloric acid or sulphuric acid.

The hydrolysis of the nitriles is in general carried out in a temperature range from −20° C. to +200° C., preferably from +20° C. to +150° C.

The esters are hydrolysed by a customary method, by treating the esters in inert solvents with customary bases, it being possible to convert the initially resulting salts into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Water or alcohols such as methanol, ethanol, propanol or isopropanol are particularly preferably used.

It is also possible to use mixtures of the solvents mentioned.

The hydrolysis is in general carried out in a temperature range from 0° C. to +140° C., preferably from +20° C. to +100° C.

In general, the hydrolysis is carried out at normal pressure. However, it is also possible to work at elevated pressure or at reduced pressure (for example from 0.5 to 5 bar).

When carrying out the hydrolysis, the base is in general employed in an amount from 1 to 10 moles, preferably from 1 to 5 moles, relative to 1 mole of the ester.

When carrying out the reaction, the carboxylates of the compounds according to the invention are formed in the first step as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. In tis connection, it has proved advantageous in the preparation of the carboxylic acids to acidify the basic reaction mixture from the hydrolysis in a second step without isolation of the carboxylates. The acids can then be isolated in a customary manner. In the case of the basic heterocycles, the salts of these heterocycles with the inorganic acids can also be obtained by treating the solutions of the carboxylates with the abovementioned acids.

The acids are esterified according to a customary method, by reacting the acids in the presence of a catalyst with the corresponding alcohols, if appropriate in one of the abovementioned solvents. Preferably, this alcohol is also employed as a solvent.

Catalysts which can be employed are inorganic acids, such as, for example, sulphuric acid or inorganic acid chlorides, such as, for example, thionyl chloride.

In general, 0.01 to 1, preferably 0.05 to 0.5 mole of catalyst is employed, relative to 1 mole of reactant.

The amidation is carried out in one of the abovementioned solvents, preferably in alcohols such as ethanol or methanol, in a temperature range from 0° C. to +80° C., preferably from +10° to +30° C., and at normal pressure.

Both the esterification and the amidation can proceed via the activated stage of the acid halides (I, Y=halogen), which can be prepared from the corresponding acid by reaction with thionyl chloride, phosphorus trichloride, phosphorus pentachloride, phosphorus tribromide or oxalyl chloride.

The compounds of the general formula (II) are new. They can be prepared by a process in which phenylhydrazines of the general formula (IIIa)

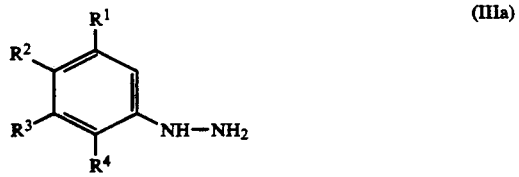

in which $R^1$, $R^2$, $R^3$ and $R^4$ have the abovementioned meaning, are reacted with cycloalkanonesulphonamides of the general formula (IV)

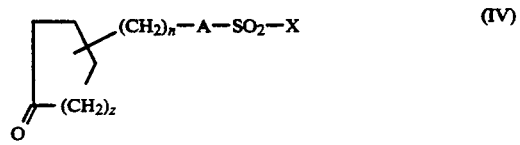

in which A, X, n and z have the abovementioned meaning, in analogy to the reaction conditions given under process [B].

Hydrazines which are employed for the process according to the invention are, for example: phenylhydrazine, 4-methoxyphenylhydrazine, 4-chlorophenylhydrazine, 4-fluorophenylhydrazine, 4-methylphenylhydrazine, 2,4-difluorophenylhydrazine, 3,5-difluorophenylhydrazine, 3-fluorophenylhydrazine and 2-fluorophenylhydrazine.

The phenylhydrazines of the general formulae (III) and (IIIa) are known in some cases or can be prepared by a customary method [compare Houben-Weyl, "Methoden der organischen Chemie" (Methods of Organic Chemistry) X/2, page 1, 123, 693; DOS 2,312,256].

The enantiomerically pure compounds of the general formula (I) according to the invention can be obtained according to customary methods, for example in analogy to the process described in DOS 3,631,824. The reduction of the cycloalkano[b]indolesulphonamides is also described there.

The cycloalkanonesulphonamides of the general formula (IV) are new and can be prepared, however, just like the known cycloalkanonecarbamides of the formula (IVa) according to the process published in DOS 3,631,824.

The sulphonyl halides of the formula (VI) can be prepared by methods which are known per se [compare Z. Talik and E. PXlazek, Acta Polon. Pharm., 12, 5 (1955).

The amines of the general formula (VIIa) are known [compare Houben-Weyl, "Methoden der organischen Chemie" (Methods of Organic Chemistry), Vol. XI/1 and XI/2].

The sulphonamides of the general formula (VIIb) are also known [compare Beilstein, 11, 26].

The cycloalkano[b]dihydroindoles and -indolesulphonamides substituted by heterocycles, their salts and isomers can be employed as active compounds in medicaments. The substances have a thrombocyte aggregation-inhibiting and thromboxane $A_2$-antagonistic action and inhibit thromboxane synthase in isolated platelets.

They can be employed for the treatment of thromboembolic disorders and ischaemias such as myocardial infarct, stroke, transitory and ischaemic attacks, angina pectoris, peripheral circulatory disorders, prevention of restenoses such as after thrombolytic therapy, percutaneous transluminal angioplasty (PTA), percutaneous transluminal coronary angioplasty (PTCA), bypass and for the treatment of arteriosclerosis, asthma and allergies.

To determine the thrombocyte aggregation-inhibiting action, blood from healthy subjects of both sexes was used. 3.8% strength aqueous sodium citrate solution was admixed to 9 parts of blood as an anticoagulant. Platelet-rich citrate plasma (PRP)[1] was obtained from this blood by means of centrifugation (Jürgens/-Beller, Klinische Methoden der Blutgerinnungsanalyse (Clinical Methods of Blood Coagulation Analysis); Thieme Verlag, Stuttgart, 1959).

For these investigations, 0.8 ml of (PRP)[1] and 0.1 ml of the active compound solution were preincubated in the water bath at 37° C. The thrombocyte aggregation was then determined by the turbidometric method (Born, G. V. R., J. Physiol, (London), 162, 67, 1962) in an aggregometer at 37° C. (Therapeutische Berichte 47, 80–86, 1975). For this purpose, 0.1 ml of collagen, an aggregation-inducing agent, was added to the preincubated sample. The change of the optical density in the sample of the (PRP) was recorded for a period of 6 minutes and the deflection determined after 6 minutes. For this purpose, the percentage inhibition compared to the control was calculated.

The range of the minimum effective concentration was given as the threshold concentration.

| Example No. | TAI threshold concentration (μg/ml) |
|---|---|
| 7 | 0.01–0.03 |
| '8 | 0.1–0.3 |
| 9 | 0.03–0.1 |
| 10 | 0.03–0.1 |
| 11 | 0.003–0.01 |
| 12 | 0.1–0.3 |

Measurement of thromboxane synthase in washed human thrombocytes.

1. Preparation of thrombocyte suspensions

Blood from healthy donors is taken up in EDTA (1% in 0.9% NaCl, 9+1) and centrifuged at 1,000 rpm (150 g) for 20 min. The platelet-rich plasma (PRP)[2] is siphoned off and in each case 10 ml is centrifuged at 2,500 rpm for 20 min. The platelet-rich plasma[2] is decanted off. The remaining platelets are suspended in 5 ml of resuspension buffer (0.15M TRIS/0.9% NaCl/77 mmol EDTA, 8:9:1; adjusted to pH 7.4 with 1N HCl), centrifuged at 2,500 rpm for 20 min and suspended in 1 ml of resuspension buffer. The thrombocyte number is adjusted to $3 \times 10^5/\mu l$.

2. Measurement of the thromboxane synthase 1 ml of the platelet suspension and 0.01 ml of the test preparation in 10% DMSO are incubated at 37° C. for 2 min. 0.1 ml of $^3$H-arachidonic acid from Amersham Buchler GmbH and Co. KG ($6.6 \times 10^{-5}$ mol/l) having a specific activity of 140 MBq/mmol are added to this and the mixture is incubated at 37° C. for a further 10 min. After the reaction, the mixture is acidified with about 0.02 ml of 0.5N citric acid and immediately extracted 3 times with 1 ml portions of ethyl acetate. The supernatants are collected in 10 ml glass tubes and the ethyl acetate is blown off at 25° C. under $N_2$. The residue is taken up in 50 μl of MeOH/CHCl$_3$ (1:1) and applied to glass TLC plates (silica gel 60, F254, 20×20 cm, Merck).

Separation is carried out in an eluant mixture of CHCl$_3$/MeOH/glacial acetic acid/H$_2$O (80:8:1:0.8). The distribution of the radioactivity is detected in a Ramona-Ls TLC scanner from Raytest and quantitatively interpreted using an integration programme.

The concentration of the test substances which leads to a 50% inhibition of thomboxane formation compared to the control is determined.

Inhibition of the thromboxane synthase in washed platelets from human blood.

Thromboxane receptor binding test in human thrombocyte membranes (a) Membrane preparation The blood taken the evening before by standard methods was centrifuged at 10° C. and 2,800 rpm for 10 min in the morning. 10 μM indomethacin was added to the Buffy coat resulting in the course of this as a layer between the platelet-poor plasma and the erythrocytes. A preparation of thrombocyte membranes was made from the Buffy coat by a method which has been described by Barber and Jamieson (compare Barber, A. J., Jamieson, G. A.: Isolation and characterization of plasma membranes from human blood platelets, J. Biol, Chem. 245, 6357–6365, 1970). As the most important step, thrombocytes are loaded with glycerol in the course in this and brought to lysis by means of osmotic shock.

The washed membranes thus obtained were resuspended in tris-NaCl-glucose buffer (50 mM tris, 100 mM NaCl, 5 mM glucose, pH 7.4), rapidly frozen in dry ice and stored at −70° C.

(b) Displacement studies

For the displacement studies, 100 μg of membrane protein and about 5 nM of $^3$H-(3R)-3-(4-fluorophenylsulphonamido)-9-(2-carboxyethyl)-1,2,3,4-tetrahydro-4α,4β-carbazole [for preparation compare DOS 3,631,824; the radioactive labelling is carried out by a method known from the literature] were incubated in a total volume of 1 ml of tris-NaCl-glucose buffer. Increasing concentrations of the displacing non-labelled compounds according to the invention dissolved in DMSO were added to the starting mixture (final concentration, 0.5% DMSO, relative to the assay volume).

The substance concentration IC$_{50}$, which is required in order to displace 50% of the specific binding, was determined with the aid of a logit-log plot according to HILL. The inhibition constant K$_I$ was determined from the IC$_{50}$ and the dissociation constants K$_D$ (determined by Scatchard analysis).

The present invention also includes pharmaceutical preparations which contain one or more compounds of the general formula (I), or which consist of one or more active compounds of the formula (I) in addition to inert, non-toxic, pharmaceutically suitable auxiliaries and excipients, and a method for the production of these preparations.

The active compounds of the formula (I) are intended to be present in these preparations in a concentration of 0.1 to 99.5% by weight, preferably of 0.5 to 95% by weight of the total mixture.

In addition to the active compounds of the formula (I), the pharmaceutical preparations may also contain other pharmaceutical active compounds.

The abovementioned pharmaceutical preparations can be prepared in a customary manner by known methods, for example with the auxiliary (auxiliaries) or excipient(s).

In general, it has proved advantageous to administer the active compound (s) of the formula (I) in total amounts of about 0.03 to about 30 mg/kg, preferably to about 5 mg/kg of body weight every 24 hours, if appropriate in the form of several individual doses, to attain the desired result.

An individual dose contains the active compound(s), preferably in amounts of 0.01 to about 10, particularly preferably 0.1 to 1.0 mg/kg of body weight.

However, it may be advantageous to deviate from the amounts mentioned, in particular depending on the type and the body weight of the subject to be treated, on individual behavior towards the medicaments, the type and severity of the disorder, the type of preparation and administration, and the time or interval at which administration takes place.

Preparation Examples

Example 1

9-(2-Ethoxycarbonylethyl)-3(R)-(4-pyridylsulphonamido)-1,2,3,4-tetrahydrocarbazole

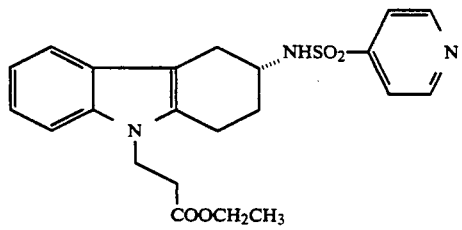

0.9 g (2.3 mmol) of 9-(2-carboxyethyl)-3(R)-(4-pyridylsulphonamido)-1,2,3,4-tetrahydrocarbazole is dissolved in 50 ml of ethanol p.a., 3 ml of concentrated sulphuric acid are added and the mixture is boiled under reflux for 1.5 hours with stirring. After cooling to room temperature, 12.0 g of sodium hydrogen carbonate are added, water is added after the evolution of gas has ended and the mixture is extracted several times with ethyl acetate. The combined organic phases are dried with sodium sulphate and the solvent evaporated therefrom. The crude product is purified by chromatography on silica gel 60 (40–63 μm, Merck, eluant: $CH_2Cl_2$:$CH_3OH$=10:1). $R_f$=0.63 ($CH_2Cl_2$:$CH_3OH$=10:1)

The examples shown in Table 1 are prepared in analogy to the procedure of Example 1:

TABLE 1

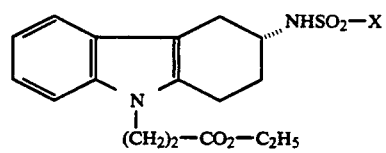

| Example No. | X | $R_f$ | Eluant |
|---|---|---|---|
| 2 | (4-pyridyl) | 0.60 | a) |
| 3 | (2-chloro-pyridyl) | 0.78 | a) |
| 4 | (chloro-methyl-thienyl) | 0.47 | b) |
| 5 | (methyl-thiazolyl) | 0.40 | c) |
| 6 | (3-pyridyl) | 0.73 | d) |

Eluant systems:
a) Toluene/ethyl acetate = 1:1
b) Methylene chloride:methanol = 100:1
c) Toluene:ethyl acetate = 2:1
d) Methylene chloride:methanol = 10:1

Example 7

9-(2-Carboxyethyl)-3(R)-(4-pyridylsulphonamido)-1,2,3,4-tetrahydrocarbazole

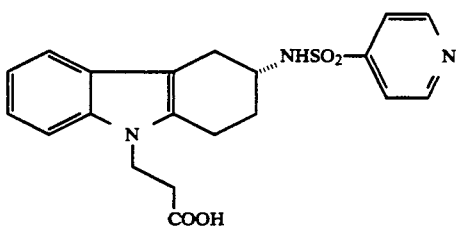

1.3 g (3.4 mmol) of 9-(2-cyanoethyl)-3(R)-(4-pyridylsulphonylamino)-1,2,3,4-tetrahydrocarbazole are dissolved in 10 ml of ethanol, 80 ml of 10% strength sodium hydroxide solution are added and the mixture is heated to reflux for 5 hours. It is then cooled to room temperature and extracted with dichloromethane. After the removal of residual organic solvent from the aqueous phase in vacuo, the solution is cooled to 0° C. and acidified to pH=2 with hydrochloric acid, and the product obtained is filtered off with suction and washed several times with water. The product is dried in a high vacuum over phosphorus pentoxide and sodium hydroxide and purified by chromatography (silica gel 60, 40–63 μm, Merck, eluant: $CH_2Cl_2$:$CH_3OH$=10:1) $R_f$=0.30 ($CH_2Cl_2$=$CH_3OH$=10:1)

The examples shown in Table 2 are prepared in analogy to the procedure of Example 6:

TABLE 2

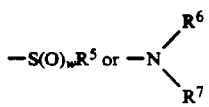

| Example No. | X | $R_f$ | Eluant |
|---|---|---|---|
| 8 | (3-pyridyl) | 0.32 | e) |
| 9 | (chloropyridyl) | 0.23 | e) |
| 10 | (chlorothienyl) | 0.08 | e) |
| 11 | (thiazolyl) | 0.36 | e) |
| 12 | (pyridyl) | 0.22 | e) |

Eluants:
e) Methylene chloride:methanol = 10:1

What is claimed is:

1. A heterocyclyl substituted cycloalkano[b]dihydroindole or -indolesulphonamide of the formula

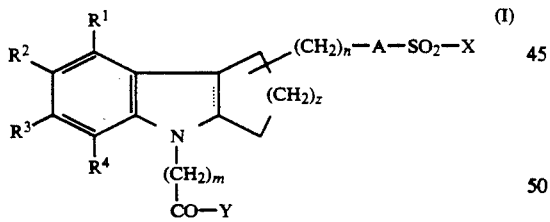

in which $R^1$, $R^2$, $R^3$ and $R^4$ are identical or different and represent hydrogen, nitro, cyano, halogen, trifluoromethyl, carboxyl, hydroxyl or trifluoromethoxy, or represent a group of the formula —S(O)$_w$R$^5$, in which
  $R^5$ denotes straight-chain or branched alkyl having up to 8 carbon atoms or aryl having 6 to 10 carbon atoms, which is optionally substituted by halogen, nitro, cyano or trifluoromethyl,
  w denotes the number 0, 1 or 2, or
  represents straight-chain or branched alkoxy or alkoxycarbonyl in each case having up to 10 carbon atoms, or benzyloxy, or
  represents a group of the formula —NR$^6$R$^7$, in which
    $R^6$ and $R^7$ are identical or different and
denote hydrogen, straight-chain or branched alkyl or acyl in each case having up to 8 carbon atoms or
denote aryl having 6 to 10 carbon atoms, or
denote a group of the formula —S(O)$_w$R$^5$, in which $R^5$ and w have the abovementioned meaning,
represent cycloalkyl having 3 to 8 carbon atoms or
represent aryl having 6 to 10 carbon atoms, or
represent straight-chain or branched alkyl or alkenyl in each case having up to 10 carbon atoms, which are optionally substituted by halogen, hydroxyl, carboxyl, cyano, aryl having 6 to 10 carbon atoms, straight-chain or branched alkyl, alkoxy or alkoxycarbonyl in each case having up to 8 carbon atoms or by a group of the formula $$-S(O)_wR^5 \text{ or } -N\begin{array}{c}R^6\\R^7\end{array}$$

in which w, $R^5$, $R^6$ and $R^7$ have the abovementioned meaning,
m represents the number 1, 2, 3 or 4,
n represents the number 0, 1 or 2,
z represents the number 1, 2, 3 or 4,
A represents a bond or the —NH group,
X represents pyridyl, pyrimidyl, pyridazyl, quinolyl, morpholinyl, piperidinyl, thienyl, pyrryl, oxazolyl, isoxazolyl, imidazolyl, thiazolyl or isothiazolyl, which are optionally monosubstituted or disubstituted by identical or different substituents selected from the group consisting of fluorine, chlorine, bromine, trifluoromethyl, trifluoromethoxy, hydroxyl or straight-chain or branched alkyl having up to 6 carbon atoms,
Y represents hydroxyl, alkoxy having up to 8 carbon atoms, phenoxy or a group of the formula —NR$^6$R$^7$, in which
  $R^6$ and $R^7$ have the abovementioned meaning, an isomeric form thereof, or a salt thereof.

2. A heterocyclyl substituted cycloalkano[b]dihydroindole or -indolesulphonamide according to claim 1 in which $R^1$, $R^2$, $R^3$ and $R^4$ are identical or different and represent hydrogen, fluorine, chlorine, bromine, iodine, nitro, cyano, trifluoromethyl, trifluoromethoxy, straight-chain or branched alkyl or alkoxy in each case having up to 6 carbon atoms, or phenyl, or represent a group of the formula —NR$^6$R$^7$, in which
  $R^6$ and $R^7$ are identical or different and
  denote hydrogen, straight-chain or branched alkyl having up to 6 carbon atoms or phenyl, or
  represent a group of the formula —S(O)$_w$R$^5$, in which
    $R^5$ denotes straight-chain or branched alkyl having up to 6 carbon atoms, or phenyl, and
    w denotes the number 0 or 2,
m represents the number 1, 2 or 3,
n represents the number 0 or 1,
z represents a number 1, 2 or 3,
A represents a direct bond or the —NH group,
X represents pyridyl, pyrimidyl, pyridazyl, quinolyl, morpholinyl, piperidinyl, thienyl, pyrryl, oxazolyl, isoxazolyl, imidazolyl, thiazolyl or isothiazolyl, which are optionally monosubstituted or disubstituted by identical or different substituents selected from the group consisting of fluorine, chlorine, bromine, trifluoromethyl, trifluoromethoxy, hydroxyl or straight-chain or branched alkyl having up to 6 carbon atoms, Y represents hydroxyl, alkoxy having up to 6 carbon atoms, phenoxy or a group of the formula $-NR^6R^7$, in which $R^6$ and $R^7$ have the abovementioned meaning, an isomeric form thereof, or a salt thereof.

3. A heterocyclyl substituted cycloalkano[b]dihydroindole or -indolesulphonamide according to claim 1 in which $R^1$, $R^2$, $R^3$ and $R^4$ are identical or different and represent hydrogen, fluorine, chlorine, trifluoromethyl or trifluoromethoxy or straight-chain or branched alkyl having up to 4 carbon atoms, m represents the number 1 or 2, n represents the number 0 or 1, z represents the number 1 or 2, A represents the —NH group, X represents pyridyl, thienyl, pyrryl, imidazolyl, isothiazolyl or thiazolyl, which are optionally substituted by fluorine, chlorine, bromine, trifluoromethyl, trifluoromethoxy or straight-chain or branched alkyl having up to 4 carbon atoms, Y represents hydroxyl, alkoxy having up to 4 carbon atoms, phenoxy or a group of the formula $-NR^6R^7$, in which $R^6$ and $R^7$ are identical or different and denote hydrogen or straight-chain or branched alkyl having up to 4 carbon atoms, an isomeric form thereof, or a salt thereof.

4. The heterocyclyl substituted cycloalkano[b]dihydroindole or -indolesulphonamide according to claim 1, which is 9-(2-carboxyethyl)-3(R)-(4-pyridylsulphonamido)-1,2,3,4-tetrahydrocarbazole having the formula

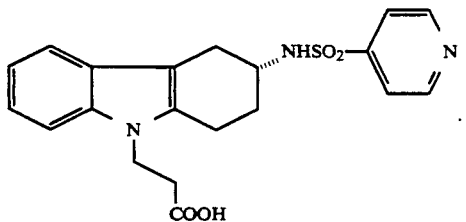

5. The heterocyclyl substituted cycloalkano[b]dihydroindole or -indolesulphonamide according to claim 1, which is 9-(2-carboxyethyl)-3(R)-(2-pyridylsulphonamido)-1,2,3,4-tetrahydrocarbazole having the formula

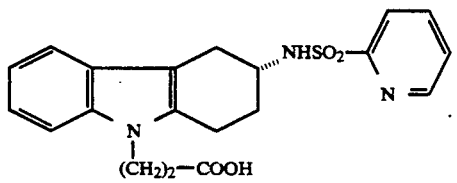

6. The heterocyclyl substituted cycloalkano[b]dihydroindole or -indolesulphonamide according to claim 1, which is 9-(2-carboxyethyl)-3(R)-(2-chloro-5-pyridylsulphonamido)-1,2,3,4-tetrahydrocarbazole having the formula

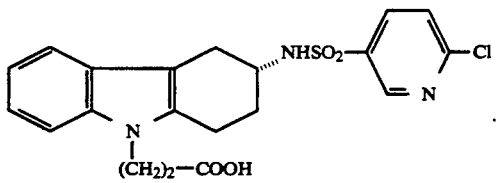

7. The heterocyclyl substituted cycloalkano[b]dihydroindole or -indolesulphonamide according to claim 1, which is 9-(2-carboxyethyl)-3(R)-(2-chloro-5-thienylsulphonamido)-1,2,3,4-tetrahydrocarbazole having the formula

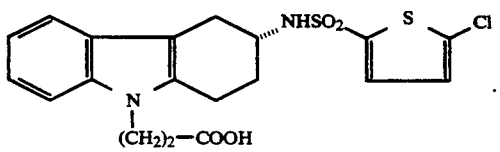

8. The heterocyclyl substituted cycloalkano[b]dihydroindole or -indolesulphonamide according to claim 1, which is 9-(2-carboxyethyl)-3(R)-(1,3-thiazol-2-ylsulphonamido)-1,2,3,4-tetrahydrocarbazole having the formula

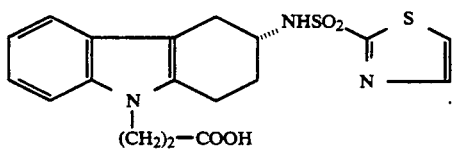

9. The heterocyclyl substituted cycloalkano[b]dihydroindole or -indolesulphonamide according to claim 1, which is 9-(2-carboxyethyl)-3(R)-(3-pyridylsulphonamido)-1,2,3,4-tetrahydrocarbazole having the formula

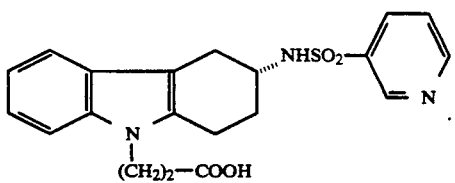

10. A composition for the treatment of thromboembolism, ischaemias, asthma and allergies comprising an amount effective therefor of a heterocyclyl substituted cycloalkano[b]dihydroindole or -indolesulphonamide according to claim 1 and a pharmaceutically acceptable carrier.

11. The composition according to claim 10 wherein the heterocyclyl substituted cycloalkano[b]dihydroindole or -indolesulphonamide is selected from the group consisting of 9-(2-carboxyethyl)-3(R)-(4-pyridylsulphonamido)-1,2,3,4-tetrahydrocarbazole, 9-(2-carboxyethyl)-3(R)-(2-pyridylsulphonamido)-1,2,3,4-tetrahydrocarbazole, 9-(2-carboxyethyl)-3(R)-(2-chloro-5-pyridylsulphonamido)-1,2,3,4-tetrahydrocarbazole, 9-(2-carboxyethyl)-3(R)-(2-chloro-5-thienylsulphonamido)-1,2,3,4-tetrahydrocarbazole, 9-(2-carboxyethyl)-3(R)-(1,3,-thiazol-2-ylsulphonamido)-1,2,3,4-tetrahydrocarbazole, or 9-(2-carboxyethyl)-3(R)-(3-pyridylsulphonamido)-1,2,3,4-tetrahydrocarbazole.

12. A method for the treatment of thromboembolisms, ischaemias, asthma and allergies in a patient, which comprises administering to the patient an effective amount therefor of a heterocyclyl substituted cycloalkano[b]dihydroindole or -indolesulphonamide according to claim 1.

13. The method according to claim 12 wherein the heterocyclyl substituted cycloalkano[b]dihydroindole or -indolesulphonamide is selected from the group consisting of 9-(2-carboxyethyl)-3(R)-(4-pyridylsulphonamido)-1,2,3,4-tetrahydrocarbazole, 9-(2-carboxyethyl)-3(R)-(2-pyridylsulphonamido)-1,2,3,4-tetrahydrocarbazole, 9-(2-carboxyethyl)-3(R)-(2-chloro-5-pyridylsulphonamido)-1,2,3,4-tetrahydrocarbazole, 9-(2-carboxyethyl)-3(R)-(2-chloro-5-thienylsulphonamido)-1,2,3,4-tetrahydrocarbazole, 9-(2-carboxyethyl)-3(R)-(,3,-thiazol-2-ylsulphonamido)-1,2,3,4-tetrahydrocarbazole, or 9-(2-carboxyethyl)-3(R)-(3-pyridylsulphonamido)-1,2,3,4-tetrahydrocarbazole.

14. A compound of the formula

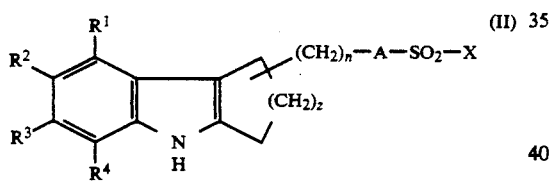

in which $R^1$, $R^2$, $R^3$ and $R^4$ are identical or different and
represent hydrogen, nitro, cyano, halogen, trifluoromethyl, carboxyl, hydroxyl or trifluoromethoxy, or
represent a group of the formula $-S(O)_wR^5$, in which
$R^5$ denotes straight-chain or branched alkyl having up to 8 carbon atoms or aryl having 6 to 10 carbon atoms, which is optionally substituted by halogen, nitro, cyano or trifluoromethyl,
w denotes the number 0, 1 or 2, or represents straight-chain or branched alkoxy or alkoxycarbonyl in each case having up to 10 carbon atoms, or benzyloxy, or represents a group of the formula $-NR^6R^7$, in which
$R^6$ and $R^7$ are identical or different and
denote hydrogen, straight-chain or branched alkyl or acyl in each case having up to 8 carbon atoms or
denote aryl having 6 to 10 carbon atoms, or
denote a group of the formula $-S(O)_wR^5$, in which $R^5$ and w have the abovementioned meaning,
represent cycloalkyl having 3 to 8 carbon atoms or
represent aryl having 6 to 10 carbon atoms, or
represent straight-chain or branched alkyl or alkenyl in each case having up to 10 carbon atoms, which are optionally substituted by halogen, hydroxyl, carboxyl, cyano, aryl having 6 to 10 carbon atoms, straight-chain or branched alkyl, alkoxy or alkoxycarbonyl in each case having up to 8 carbon atoms or by a group of the formula

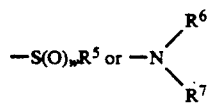

in which
w, $R^5$, $R^6$ and $R^7$ have the abovementioned meaning,
n represents the number 0, 1 or 2,
z represents the number 1, 2, 3 or 4,
A represents a bond or the —NH group,
x represents pyridyl, pyrimidyl, pyridazyl, quinolyl, morpholinyl, piperidinyl, thienyl, pyrryl, oxazolyl, isoxazolyl, imidazolyl, thiazolyl or isothiazolyl, which are optionally monosubstituted or disubstituted by identical or different substituents selected from the group consisting of fluorine, chlorine, bromine, trifluoromethyl, trifluoromethoxy, hydroxyl or straight-chain or branched alkyl having up to 6 carbon atoms,
Y represents hydroxyl, alkoxy having up to 8 carbon atoms, phenoxy or a group of the formula $-NR^6R^7$, in which
$R^6$ and $R^7$ have the abovementioned meaning.

* * * * *

UNITED STATES PATENT AND TRADEMARK OFFICE
CERTIFICATE OF CORRECTION

PATENT NO. : 5,204,374

DATED : April 20, 1993

INVENTOR(S) : Muller, et al.

It is certified that error appears in the above-identified patent and that said Letters Patent is hereby corrected as shown below:

Col. 21, line 29   After " 3(R)-( " insert -- 1 --

Signed and Sealed this

Sixth Day of September, 1994

Attest:

BRUCE LEHMAN

*Attesting Officer*     *Commissioner of Patents and Trademarks*